US005744349A

United States Patent [19]
Piwnica-Worms

[11] Patent Number: 5,744,349
[45] Date of Patent: Apr. 28, 1998

[54] DNA SEQUENCES ENCODING HUMAN MYT1 KINASE

[75] Inventor: Helen Piwnica-Worms, Ladue, Mo.

[73] Assignee: Washington University, St. Louis, Mo.

[21] Appl. No.: 610,731

[22] Filed: Mar. 5, 1996

[51] Int. Cl.$^6$ .................................................. C12N 15/54
[52] U.S. Cl. .............................. 435/252.3; 435/254.11; 435/194; 536/23.2
[58] Field of Search .......................... 435/252.3, 254.11, 435/194; 536/23.2

[56] References Cited

PUBLICATIONS

Gautier et al., Cdc25 is a Specific Tyrosine Phosphatase That Directly Activates p34$^{cdc2}$. *Cell.* 67:197–211 (1991).

Guan et al., "Isolation and Characterization of a Novel Dual Specific Phosphatase, HVH2, Which Selectively Dephosphorylates the Mitogen–Activated Protein Kinase." *J. Biol. Chem.* 270(13):7197–7203 (1995).

Honda et al., "Dephosphorylation of Human p34$^{cdc2}$ Kinase on Both Thr–14 and Tyr–14 by Human Cdc25B Posphatase." *FEBS Letters.* 318(3):331–334 (1993).

Kornbluth et al., "Membrane Localization of the Kinase Which Phosphorylates p34$^{cdc2}$ on Theonine 14" *Mol. Biol. Of the Cell.* 5:273–282 (1994).

Kuang et al., "Cdc25 is One of the MPM–2 Antigens Involved in the Activation of Maturation–Promoting Factor." *Mol. Biol. Of the Cell.* 5:135–145 (1994).

Lee et al., Cdc25$^+$ Encodes a Protein Phosphatase That Dephosphorylates p34$^{cdc2}$. *Mol. Biol. of the Cell.* 3:73–84 (1992).

Millar et al., "Cdc25 M–Phase Inducer." *Cold Spring Harbor Symposia on Quantitative Biology.* 56:577–584 (1991).

Mueller et al., "Cell Cycle Regulation of a Xenopus Wee1–like Kinase." *Mol. Biol. of the Cell.* 6:119–134 (1995).

Parker et al., "Identification of a 95–kDa WEE1–like Tyrosine Kinase in HeLa Cells." *Proc. Nat'l Acad. Sci. USA.* 92:9638–9642 (1995).

Sebastian et al., "Cdc25M2 Activation of Cyclin–dependent Kinases by Dephosphorylation of Theonine–14 and Tyrosine–15." *Proc. Nat'l. Acad. Sci. USA.* 90:3521–3524 (1993).

Science, 25 Sep. 1992, vol. 257, pp. 1955–1957; "Inactivation of the p34$^{cdc2}$–Cyclin B Complex by the Human WEE 1 Tyrosine Kinase"; Laura L. Parker and Helen Piwnica-Worms.

Molecular Biology of the Cell, Sep. 1994, vol. 5, pp. 989–1001; "Cell Cycle Regulation of the p34$^{cdc2}$ Inhibitory Kinases"; Sue Atherton–Fessler et al.

Science, 6 Oct., 1995, vol. 270, pp. 86–90; Myt1: A Membrane–Associated Inhibitory Kinase That Phosphorylates Cdc2 on Both Threonine–14 and Tyrosine–15; Paul R. Mueller et al.

*Primary Examiner*—Charles L. Patterson, Jr.
*Attorney, Agent, or Firm*—Greenlee Winner and Sullivan PC

[57] ABSTRACT

The invention provides isolated, purified and structurally defined DNA encoding Myt1Hu, isolated and purified Myt1Hu protein, a method for making Myt1Hu protein by expressing the DNA encoding Myt1Hu and methods for measuring levels of Myt1Hu in RNA or of Myt1Hu in a cell sample.

6 Claims, 11 Drawing Sheets

Fig. 2

Human Myt1 Protein Sequence

```
MLERPPALAM  PMPTEGTPPP  LSGTPIPVPA  YFRHAEPGFS
LKRPRGLSRS  LPPPPPAKGS  IPISRLFPPR  TPGWHQLQPR
RVSFRGEASE  TLQSPGYDPS  RPESFFQQSF  QRLSRLGHGS
YGEVFKVRSK  EDGRLYAVKR  SMSPFRGPKD  RARKLAEVGS
HEKVGQHPCC  VRLEQAWEEG  GILYLQTELC  GPSLQQHCEA
WGASLPEAQV  WGYLRDTLLA  LAHLHSQGLV  HLDVKPANIF
LGPRGRCKLG  DEGLLVELGT  AGAGEVQEGD  PRYMAPELLQ
GSYGTAADVF  SLGLTILEVA  CNMELPHGGE  GWQQLRQGYL
PPEFTAGLSS  ELRSVLVMML  EPDPKLRATA  EALLALPVLR
QPRAWGVLWC  MAAEALSRGW  ALWQALLALL  CWLWHGLAHP
ASWLQPLGPP  ATPPGSPPCS  LLLDSSLSSN  WDDDSLGPSL
SPEAVLARTV  GSTSTPRSRC  TPRDALDLSD  INSEPPRGSF
PSFEPRNLLS  LFEDTLDPT
```

Figure 3: Sequence Comparisons Between Members of the Wee1 Family of Protein Kinases Fig. 3A: Entire Sequence Percent Identity

|    | 1    | 2    | 3    | 4    | 5    | 6    | 7    | 8    | 9    | 10   |                    |
|----|------|------|------|------|------|------|------|------|------|------|--------------------|
| 1  | ***  | 45.6 | 21.0 | 17.2 | 17.2 | 19.6 | 19.2 | 19.6 | 15.8 | 15.0 | 1. Myt1 Hu         |
| 2  | 47.6 | ***  | 13.9 | 14.2 | 14.4 | 15.1 | 17.3 | 18.2 | 14.6 | 15.1 | 2. Myt1 Xe         |
| 3  | 68.2 | 71.4 | ***  | 87.6 | 89.5 | 46.8 | 30.5 | 14.2 | 14.4 | 14.6 | 3. Wee1 Hu         |
| 4  | 67.7 | 70.8 | 10.1 | ***  | 95.8 | 45.5 | 30.7 | 16.4 | 13.1 | 16.0 | 4. Wee1 murine     |
| 5  | 67.2 | 70.5 | 8.2  | 4.0  | ***  | 46.2 | 30.7 | 16.4 | 13.8 | 15.3 | 5. Wee1 rat        |
| 6  | 69.0 | 71.3 | 47.2 | 48.7 | 47.6 | ***  | 32.6 | 13.7 | 13.3 | 13.1 | 6. Wee1 Xe         |
| 7  | 71.8 | 72.5 | 57.6 | 58.0 | 58.2 | 60.1 | ***  | 13.6 | 12.1 | 14.6 | 7. Wee1 Dros.      |
| 8  | 70.6 | 71.0 | 77.3 | 77.8 | 77.8 | 77.2 | 75.5 | ***  | 22.4 | 27.7 | 8. Wee1 S. pombe   |
| 9  | 76.8 | 77.6 | 80.9 | 81.1 | 80.9 | 80.6 | 79.4 | 69.5 | ***  | 21.2 | 9. Swe1 S. cerevisiae |
| 10 | 71.0 | 72.2 | 79.3 | 79.5 | 78.9 | 77.3 | 76.6 | 65.6 | 71.0 | ***  | 10. Mik1 S. pombe  |

Fig. 3B: Catalytic Domains

Percent Identity

|   | 1    | 2    | 3    | 4    | 5    |                         |
|---|------|------|------|------|------|-------------------------|
| 1 | ***  | 63.8 | 34.9 | 31.7 | 31.7 | 1. Myt1 Hu 104-321      |
| 2 | 34.9 | ***  | 33.3 | 32.0 | 29.7 | 2. Myt1 Xe 97-315       |
| 3 | 57.9 | 59.9 | ***  | 27.0 | 27.9 | 3. Wee1 S. pombe 560-781 |
| 4 | 63.1 | 62.8 | 65.9 | ***  | 71.7 | 4. Wee1 Xe 204-443      |
| 5 | 62.1 | 64.7 | 65.0 | 28.3 | ***  | 5. Wee1 Hu 293-532      |

DNA SEQUENCES ENCODING HUMAN MYT1 KINASE

The U.S. Government has certain rights in the invention based upon research support provided by National Institutes of Health Grant No. GM 47017.

FIELD OF THE INVENTION

The invention relates to nucleotide sequences encoding a protein known to function in regulating cell division.

BACKGROUND OF THE INVENTION AND PRIOR ART

The cells of eukaryotes, including humans and other mammals, replicate themselves by carrying out an ordered sequence of events, which are cyclically repeated in each successive cell division. In somatic (non germ-line) cells, a typical cycle has four characterized phases: G1, an interval following the completion of mitosis, also termed first gap phase; S, a period during which the cell undergoes DNA synthesis; G2 or second gap phase following completion of DNA synthesis and preceding mitosis; and M, mitosis, where separation of complete sets of replicated DNA occurs. The end result of this process is the generation of two daughter cells that are equivalent both in genetic makeup and in size to the original parent cell. A complex series of biochemical interactions act to control the cell cycle through a series of checkpoints or gating reactions which function to ensure that the requisite precursor phases are completed before the ensuing phase begins. In particular, the checkpoints ensure accurate reproduction and dispersion of the cell's genetic material. In a metazoan organism with differentiated tissues, such as a human being, cells of different tissues replicate at vastly different rates at different life stages. Early embryonic cells replicate rapidly and synchronously, whereas at later stages of development and during adulthood, some cells, such as muscle and nerve cells stop replicating while others, such as epithelial cells, continue to divide throughout the organism's life. Failure of cells to precisely control their replicative state therefore leads to a variety of diseases of pathological proliferation, including cancers and atherosclerosis.

Progress over the past several years has greatly advanced the general understanding of the biochemical reactions which regulate the cell cycle. A general paradigm for cell cycle regulation has emerged in which complexes composed of cyclins and cyclin-dependent kinases (CDKs) regulate progression through stages of the cell cycle. Several mechanisms exist to keep the activity of the cyclin/CDK complexes turned off until the appropriate stage of the cell cycle. Known mechanisms include reversible phosphorylation, binding to small molecular weight inhibitors, transcription control, intracellular location and protein degradation. In yeast, there are multiple cyclins but only a single CDK. The CDK of fission yeast is encoded by the cdc 2 gene, that of budding yeast by the CDC28 gene. In higher eukaryotes, including humans, there are multiple CDKs as well as multiple cyclins. Despite the greater complexity of the higher eukaryotes, the overall scheme for cell cycle progression involving cyclins and CDKs is conserved. Deregulation of components of these regulatory pathways has been implicated in human cancer. For a recent general review, see Hunter, T. et al. (1994) Cell 79:573–582.

Kinase is the term applied to a class of enzyme-catalyzed reactions, many of which are well-known and described in standard collegiate biochemistry texts. In general, the reaction can be abbreviated as

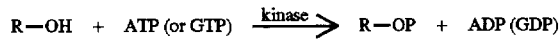

where R-OH denotes a protein or peptide having a free hydroxyl side chain (from a serine, tyrosine or threonine residue), ATP and GTP are adenosine triphosphate and guanosine triphosphate, respectively, R-OP is the protein or peptide having the free hydroxyl replaced by a phosphate ester, ADP and GDP are adenosine and guanosine diphosphate, respectively. The reaction is termed a phosphorylation reaction, the product R-OP is termed the phosphorylated form of R. The phosphate ester may be subject to enzyme-catalyzed hydrolysis, the enzymes catalyzing such hydrolysis being termed phosphatases. The phosphatase catalyzed reaction can be diagrammed as

where Pi denotes an inorganic phosphate ion. A critical feature of the phosphatase and kinases discussed herein is their extreme specificity. A given kinase is often specific only for generating a phosphate ester on a single amino acid residue on a single protein. The same can be true of a phosphatase.

Of particular importance herein is the regulation of entry into mitosis: passage from G2 to M. The Cdc2 kinase must be enzymatically active to catalyze the phosphorylation of several cellular proteins, some structural and others regulatory. The combined functions of these phosphorylated proteins lead to exit from G2 and entry into mitosis.

Early in the cell cycle, Cdc2 exists in an underphosphorylated, monomeric form that is inactive as a protein kinase. As cells progress into S-phase, cyclin B accumulates and assembles with Cdc2 to form a complex, also inactive, but subject to phosphorylation itself. Three sites on the Cdc2 moiety of the Cdc2/cyclin B complex are of functional significance when phosphorylated: tyrosine 15, threonine 14 and threonine 161. Phosphorylation of the latter (Thr 161) activates the Cdc2/cyclin B complex. The enzyme that phosphorylates at Thr 161 is termed CAK/M015. However, phosphorylation at Thr 14 and Tyr 15 overrides the activation effect of phosphorylation at Thr 161, so that the complex phosphorylated at all three sites remains enzymatically inactive. In late G2, a specific phosphatase (Cdc 25) removes phosphates at Thr 14 and Tyr 15 (but not Thr 161), generating an active Cdc2/cyclin B complex which then initiates the phosphorylation of other proteins that results in entry into mitosis.

The human Cdc2/cyclin B complex is phosphorylated at both Tyr 15 and Thr 14. The human Wee 1 kinase was found to be unable to phosphorylate Cdc2/cyclin B at Thr 14. Another enzyme was therefore responsible for the phosphorylation at Thr 14 (Parker, L. L. et al. (1992) Science 257:1955–1957). Subsequently, that enzyme was identified as a dual-specificity kinase, able to phosphorylate at both Thr 14 and Tyr 15 on Cdc2/cyclin B. The enzyme was partially purified (Atherton-Fessler, S. et al. (1994) Mol. Biol. Cell 5:989–1001).

The present invention relates to the cloning of the human DNA encoding the dual specificity kinase of Tyr 15, Thr 14 on Cdc2/cyclin B, now termed Myt1Hu. A recent paper describing a Myt1 cDNA of Xenopus has been published by Mueller, P. R., et al. (1995) Science 270:86–90.

SUMMARY OF THE INVENTION

The cDNA of the human Myt1 kinase (Myt1Hu), which catalyzes phosphorylation of Cdc2 on Thr 14 and Tyr 15, has been cloned and sequenced. The invention provides isolated, purified and structurally defined DNA encoding Myt1Hu, isolated and purified Myt1Hu protein, a method for making Myt1Hu protein by expressing the DNA encoding Myt1Hu and methods for measuring levels of Myt1Hu in RNA or of Myt1Hu protein in a cell sample. Studies comparing levels of Myt1Hu mRNA in normal and cancerous cells have revealed significant differences between normal cell and several different human cancer cell lines. Such measurements are therefore useful for detecting the presence of cancer or other disorders of cell proliferation.

BRIEF DESCRIPTION OF THE FIGURES

FIG. 2. Predicted amino acid sequence of human Myt1. The nucleotide sequence of the Myt1Hu cDNA (SEQ ID NO:1) is predicted to encode a protein 499 amino acids. The kinase domain is shown boxed. A putative membrane-localization motif is shown underlined. Arrows indicate the regions used to design the degenerate pcr primers.

FIG. 3. Sequence comparisons of human Myt1 with other members of the Wee1 family of protein kinases. (A) Identity between Myt1 and other members of the Wee1 family of protein kinases. (B) Identity between the catalytic domain of Myt1Hu with the catalytic domains of other members of the Wee1 family of protein kinases.

FIGS. 6A, 6C and 6E are phase contrast photomicrographs of transfected cells. The subcellular location of tagged Myt1Hu was determined by indirect immunofluorescence using monoclonal antibody to the myc epitope sequence. FIGS. 6B, 6D and 6F are immunofluoroescence photomicrographs of the same transfected cells labeled to reveal the intracellular location of the respective Myt 1 expression products.

DETAILED DESCRIPTION OF THE INVENTION

Figure 1:
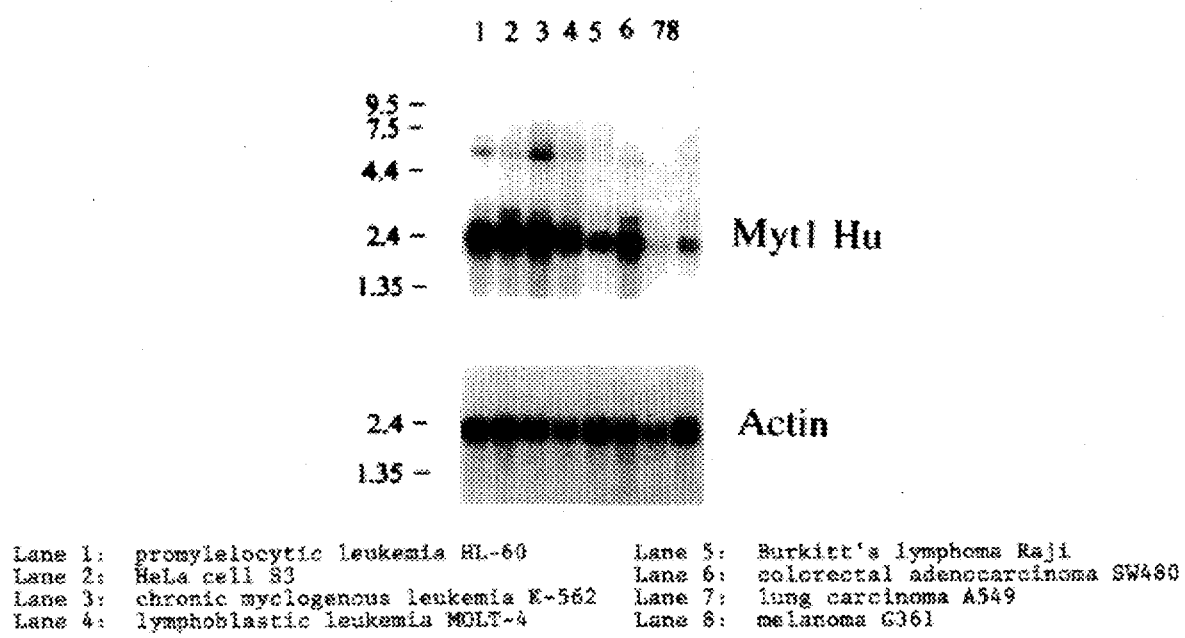
FIG. 1. Northern analysis of human Myt1. Top panel: mRNA from the following human cancer cell lines was probed with human myt1 cDNA: promyelocytic leukemia HL-60 (lane 1); HeLa cell S3 (lane 2); chronic myelogenous leukemia K-562 (lane 3); lymphoblastic leukemia MOLT-4 (lane 4); Burkitt's lymphoma Raji (lane 5); colorectal adenocarcinoma SW 480 (lane 6) ; lung carcinoma A549 (lane 7); melanoma G361 (lane 8). Bottom panel: The human myt1 probe was removed and the blot described above was hybridized with labeled human β-actin probe.

Definitions—The following terms are defined herein for convenience and clarity in describing and claiming the invention.

Kinase is an enzyme which catalyzes transfer of a phosphate group from a high energy form of phosphate, such as adenosine triphosphate (ATP) or guanosine triphosphate (GTP) to an acceptor group such as a hydroxyl. The acceptor is said to be phosphorylated. Protein kinases are enzymes which act to phosphorylate an acceptor group on a protein, notably a hydroxyl of serine, threonine or tyrosine. Many protein kinases are very specific in that the acceptor substrate can be one particular hydroxyl group on one particular protein.

Some acceptor proteins become activated by phosphorylation, others inactivated. As noted for Cdc2, phosphorylation at Thr 161 activates its function (it also becomes a kinase when activated), but phosphorylation at Thr 14 and/or Tyr 15 overrides the activation and results in inactivation.

Myt1Hu is a protein kinase which catalyzes the phosphorylation of the Thr 14 and Tyr 15 moieties of Cdc2 when the latter is present in a Cdc2/cyclin B complex. The human enzyme has dual specificity, i.e., it catalyzes phosphorylation of both Thr 14 and Tyr 15 on Cdc2. A similar enzyme of Xenopus appears to have similar specificity. The ability to catalyze phosphorylation of Cdc2 is termed Cdc2 kinase activity herein.

Phosphatase is a general term for an enzyme that catalyzes hydrolysis of a phosphate ester. Many highly specific protein phosphatases are known to function as regulators of activity, acting in concert with kinases to fine tune the activity of cellular processes.

DNA Sequence is the term used herein to denote a sequence of polydeoxynucleotides containing genetic information. Both cDNA (obtained by copying messenger RNA) and genomic DNA are included in the term "DNA sequence." Many DNA sequences are originally cloned as cDNA. Once a cDNA clone is available, genomic DNA can be obtained without undue experimentation, by techniques known in the art. For most eukaryotic genes, genomic DNA includes sequences not found in cDNA. These include introns, regulatory regions, polyadenylation signals and the like. By convention, DNA sequences are written in the direction from the 5' end to the 3' end of that strand whose sequence is that of the corresponding messenger RNA, sometimes called the "sense" strand.

Expression is the term used to denote processes by which the information content of a DNA sequence is converted to an observable function. Typically, the term refers to transcription (mRNA synthesis) and/or translation (encoded protein synthesis) of coding regions. However, non-coding regions can also be expressed, usually resulting in a regulatory effect. When a cloned DNA sequence is expressed in a heterologous cell, the expression can either be direct (where only sequences contained within the cloned DNA sequence are translated) or through synthesis of a fusion protein (including translation of an additional coding sequence). A sequence is "expressible" when combined in appropriate orientation and position with respect to control sequences (promoter, ribosome binding site, polyadenylation site, etc.) that are operative in the desired host cell as is well-known in the art.

Coding refers generally to the relationship between the nucleotide sequence of a DNA segment, and the amino acid sequence to which it corresponds, according to the known relationship of the genetic code. As is well known, a sequence of three nucleotides (triplet) encodes a single amino acid. Each of the twenty principal amino acids is encoded by at least one triplet, and most are encoded by more than one. Consequently, a single amino acid sequence can be encoded by a large number of different triplets. All the DNA sequences that encode the same amino acid sequence (synonymous codings) are therefore equivalent, although certain individual sequences may prove advantageous in certain types of host cells. Once a single coding sequence has been cloned, a person of ordinary skill in the art can readily make equivalent synonymous sequences by known methods, without undue experimentation. As used herein, a DNA sequence is said to encode a given amino acid sequence if it includes a nucleotide sequence that is translatable to the corresponding amino acid sequence. The coding nucleotide sequence may also include one or more introns, as well as untranslated nucleotide sequences, and sequences encoding other amino acid sequences.

Chimeric is a term describing a non-naturally occurring combination of two or more different DNA sequences expressible as a single amino acid sequence, a chimeric protein. The source of the different sequences can be from the same or different species or from synthetic, non-naturally occurring sequences. A chimeric protein can have separate functions attributable to the different sequences, or the different sequences can contribute to a single function. An example of the former is given herein for synthesis of cDNA encoding a myc epitope at the N-terminus of Myt1Hu. The expressed chimeric myc-Myt1Hu protein combines the functions of Myt1Hu with ability to bind to an anti-myc antibody. An example of a chimeric protein where the different parts contribute a single function would be a Xenopus-human hybrid Myt1 or other interspecies hybrid, or even a combination of a non-naturally-occurring sequence substituted for a portion of Myt1Hu. Typical chimeric amino acid sequences of the invention will include the Myt1Hu sequence combined with an added sequence that provides an additional function, e.g., where the added amino acid sequence is an epitope, has catalytic activity, is a cellular localization signal or confers a specific binding property. It will be understood that the foregoing functions need not be mutually exclusive. A specific binding property can, for example, be the specific binding of a substrate associated with catalytic (enzyme) activity or it could be the property of binding an antibody or it could simply be the ability to bind to an affinity chromatography ligand. A cellular localization signal can result in concentration of the chimeric amino acid sequence in the cell nucleus, on the endoplasmic reticulum, into an organelle or in transport to the cell exterior. Amino acid sequences conferring such properties are known in the art.

Heterologous is a term applied to an in vivo expression system where the host cells are of a different species than the DNA sequence expressed. An example herein is given by the expression of Myt1Hu in cultured insect cells. Typically, use of a heterologous expression system requires combining the coding sequence with a control sequence known to function in the heterologous host cell (a heterologous control sequence). Where Myt1Hu is expressed in insect cells, a baculovirus promoter (from an insect-pathogenic virus) is provided as the control region.

Control sequence is the term used for an untranslated DNA sequence that can function to insure expression, affect rate of expression, lifetime of mRNA and the like. Examples of control sequences include promoters, operators, enhancers, ribosome binding sites, polyadenylation signals and the like, as known in the art.

Non-human is used to denote a sequence known to have a source from a species other than human, including a synthetic source.

Antibody is used herein to include both monoclonal and polyclonal antibodies as well as antibody fragments. An antibody is "specifically reactive" with a protein or epitope if it binds with the protein or epitope preferentially compared to other proteins or epitopes which may be present in the same mixture. An antibody can be "cross-reactive" with another (usually similar) protein or epitope. However, under equilibrium conditions, antibody will be more strongly bound to a protein or epitope to which it is specifically reactive than to one to which it is merely cross-reactive.

A PCR (polymerase chain reaction) based approach using degenerate primers in combination with mRNA (prepared from Jurkat cells) was used to obtain novel members of the Wee 1 family of protein kinases. The degenerate primers were based on sequence similarities between members of the Wee 1 family of protein kinases. PCR products of the predicted molecular weight were sequenced and fell primarily into two classes: the predominant class was identical in sequence to human p95Wee1. The second class revealed a high degree of similarity to a recently reported cDNA derived from Xenopus oocytes (denoted Myt1 for membrane-associated, tyrosine- and threonine-specific, Cdc2 inhibitory kinase). The PCR product was used to screen a HeLa cell library and the corresponding full length cDNA was obtained, sequenced and its protein product was biochemically characterized. We have named this kinase human Myt1 (Myt1Hu).

The longest cDNA obtained during the library screening was ~1.9 kb. Evidence that this was a full length cDNA is suggested by the presence of a termination codon upstream of and in-frame with the assigned open reading frame. In addition, Northern analysis performed using several human cancer cell lines revealed an mRNA of ~2.2 kb (FIG. 1). Interestingly, great variability in the levels of Myt1 mRNA were detected in the various cancer cell lines. Lowest levels were detected in A549 (lung carcinoma), G361 (melanoma) and Raji (Burkitt's lymphoma) cells, respectively.

The predicted open reading of human Myt1 shown in SEQ ID NO:1 encodes a protein of 499 amino acids (SEQ ID NO:2). C-terminal to the catalytic domain amino acids 104–321 (SEQ ID NO:2) is a sequence of 20 hydrophobic/polar amino acids 379–398 (SEQ ID NO:2) bordered by an arginine and histidine. This sequence may account for the membrane localization of human Myt1 as C-terminal truncations removing this region result in the redistribution of Myt1Hu in HeLa cells (see below). A sequence comparison of the complete Myt1Hu protein sequence with other members of the Wee1 family of protein kinases indicated it is most similar to Xenopus Myt1 (46% identical, FIG. 3A). If one compares the kinase domains of human and Xenopus Myt1 the identity is even greater (~64%) (FIG. 3B). A detailed comparison of the Xenopus and human Myt1 proteins is shown in Liu, F. et al. (1997) *Molec. and Cell. Biol.* 17(2):571–583, 575.

Figure 4:
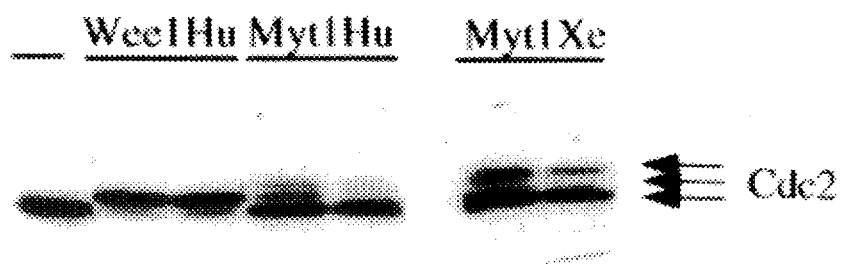
FIG. 4. Myt1Hu phosphorylates Cdc2 on Thr 14 and Tyr 15 in a cyclin-dependent manner. Sf9 cells were infected with recombinant baculoviruses encoding GST-cyclin B and Cdc2K33R alone (lane 1) or together with two concentrations of baculovirus encoding human p95Wee1 (lanes 2,3); human Myt1 (lanes 4,5) or Xenopus Myt1 (lanes 6,7). Cells were lysed and proteins were resolved on a 12% SDS polyacrylamide gel. After transfer to nitrocellulose the blot was probed with Cdc2 antisera and developed with an ECL Western blotting detection kit (Amersham).
Figure 5:
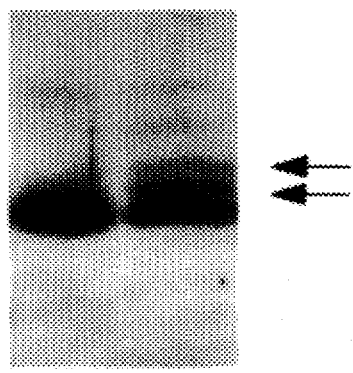
FIG. 5. Myt1Hu phosphorylates Cdc2 on Thr 14 and Tyr 15 in a cyclin-dependent manner. Uninfected Sf9 cells (lane 1) or cells infected with recombinant baculovirus encoding histidine-tagged Myt1Hu (lane 2) were lysed and lysates were incubated with nickel-NTA beads (Qiagen). Beads were washed and then kinase reactions were performed in the presence of purified Cdc2/cyclinB complex. Reactions were stopped by the addition of SDS sample buffer. Proteins were resolved on a 12% SDS-polyacrylamide gel. After transfer to nitrocellulose the blot was probed with Cdc2 antisera and developed with an ECL Western blotting detection kit (Amersham).
Figure 6A:
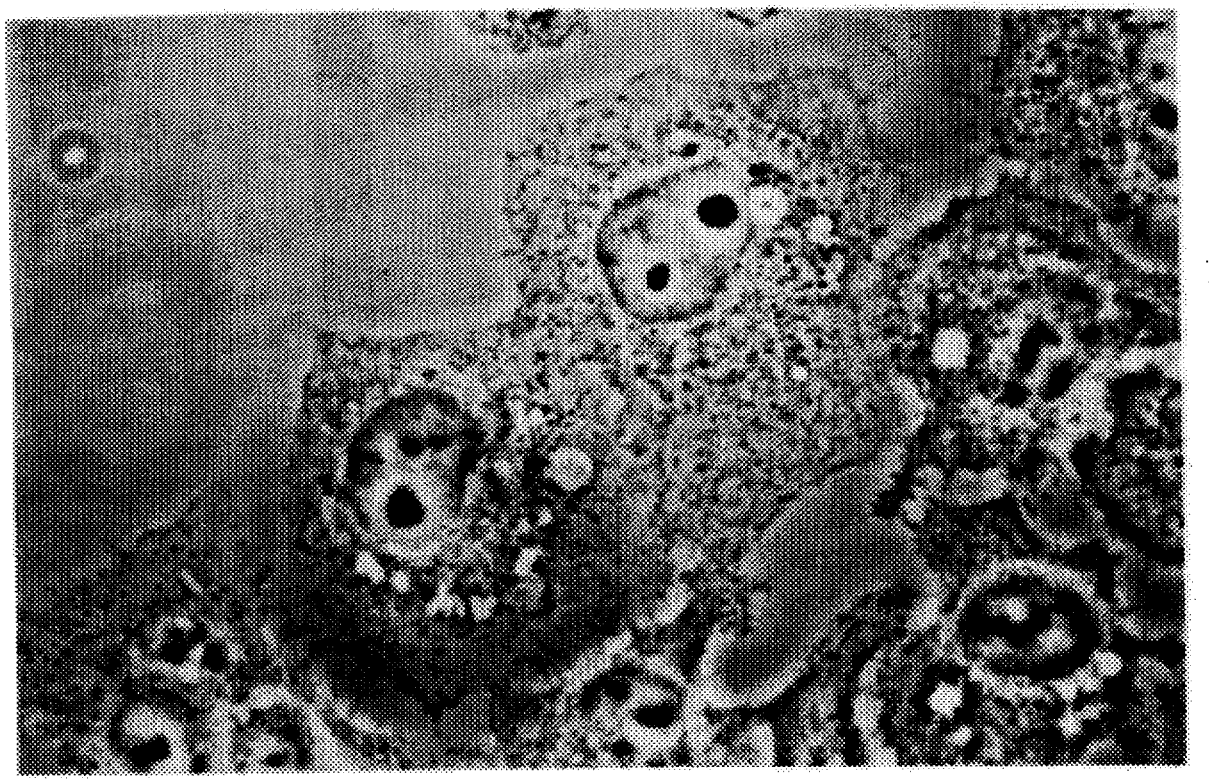
FIGS. 6A–6F. Myt1Hu localizes to the endoplasmic reticulum in HeLa cells. Myc-tagged human Myt1 (FIGS. 6A and 6B) and C-terminal deletions of 97 amino acids (FIGS. 6C and 6D) and 137 amino acids (FIGS. 6E and 6F) were transfected into HeLa cells.
Figure 6B:
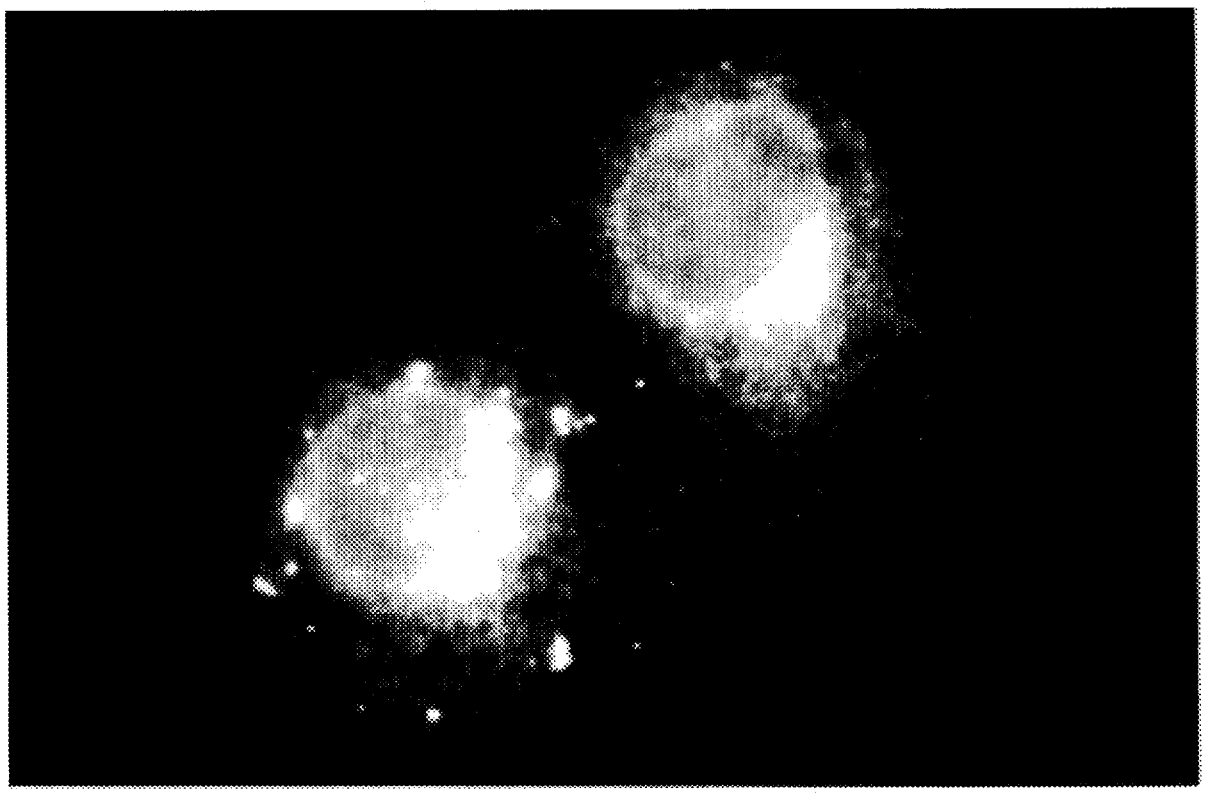
Figure 6C:
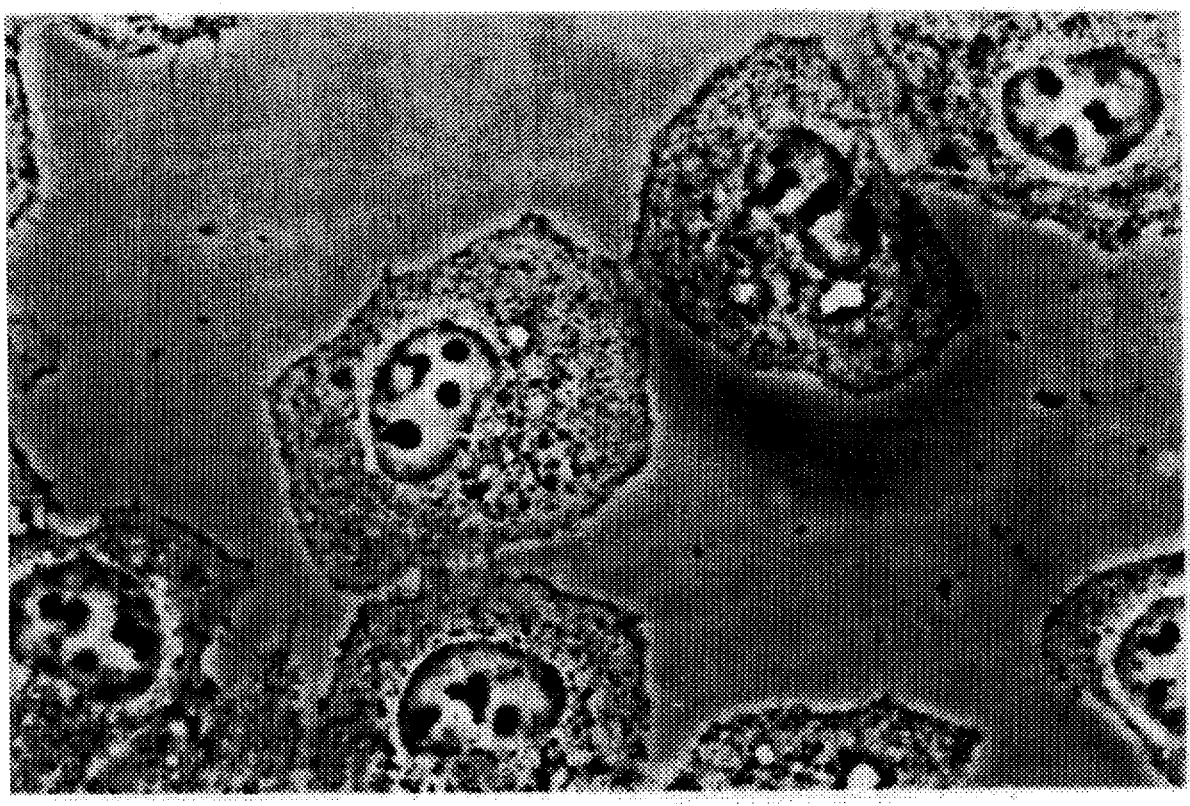
Figure 6D:
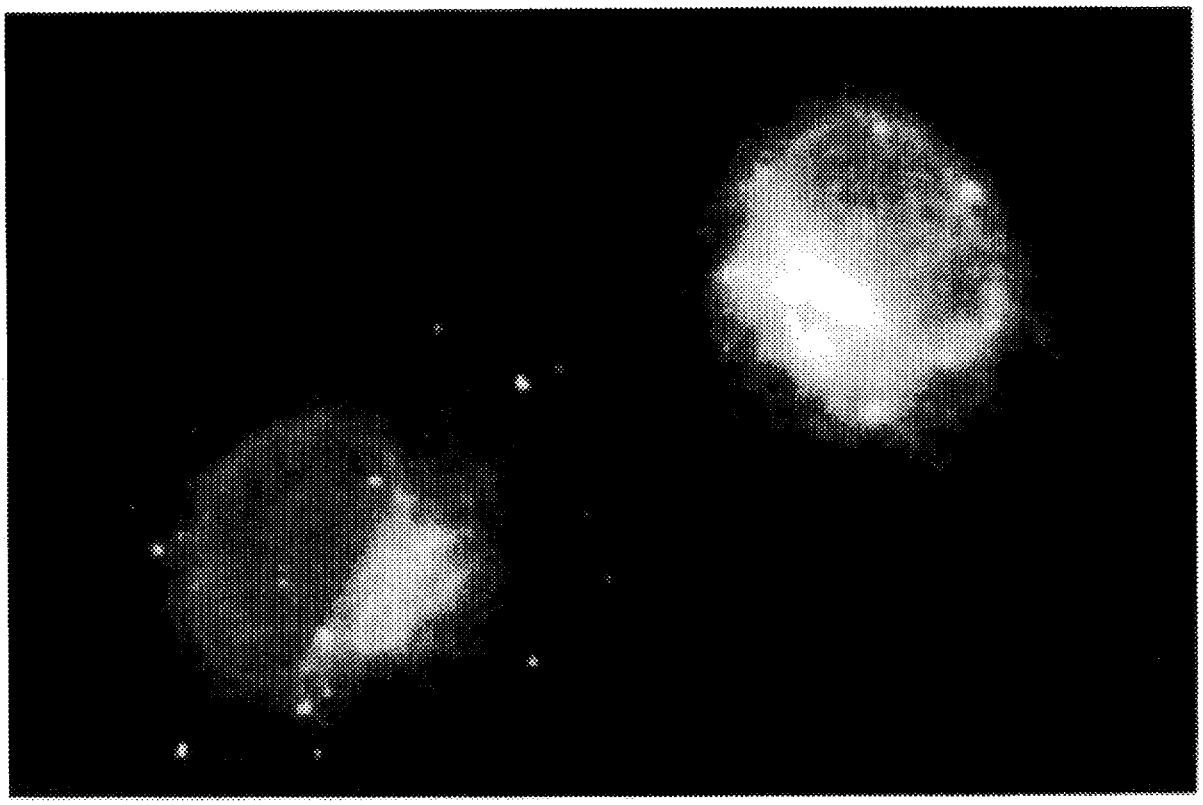
Figure 6E:
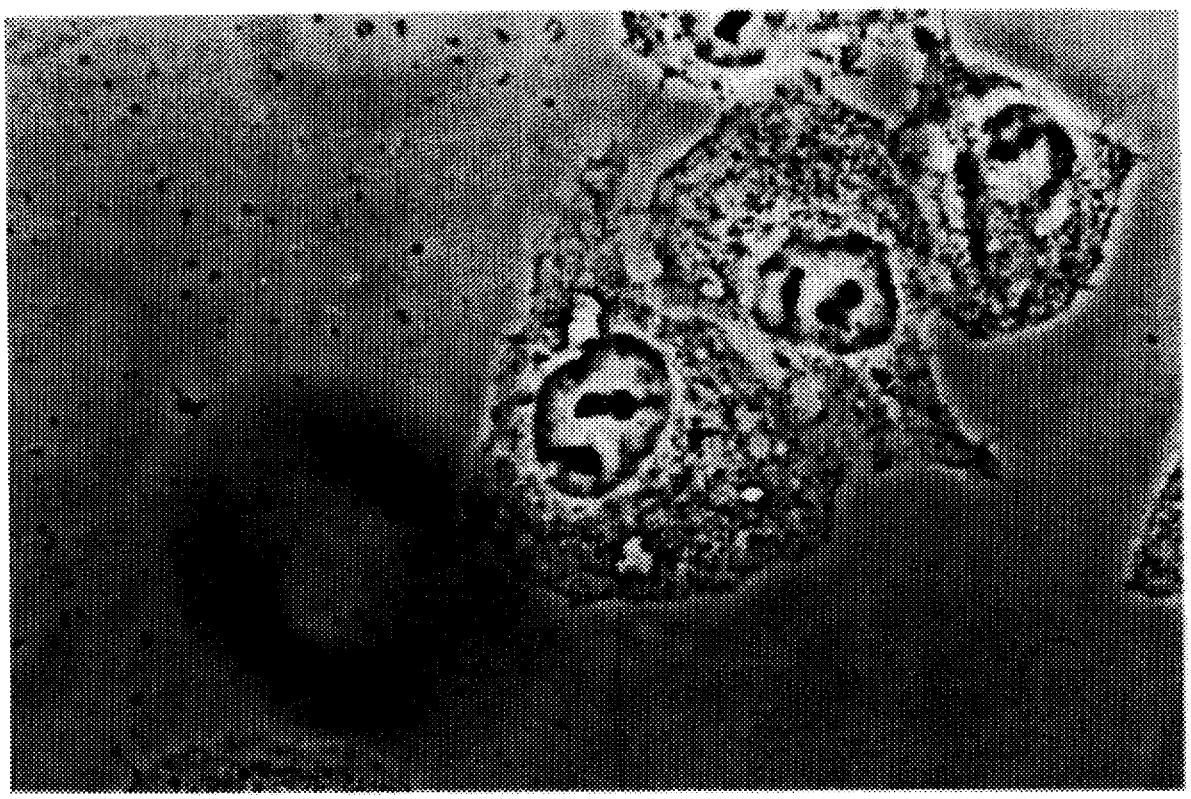
Figure 6F:
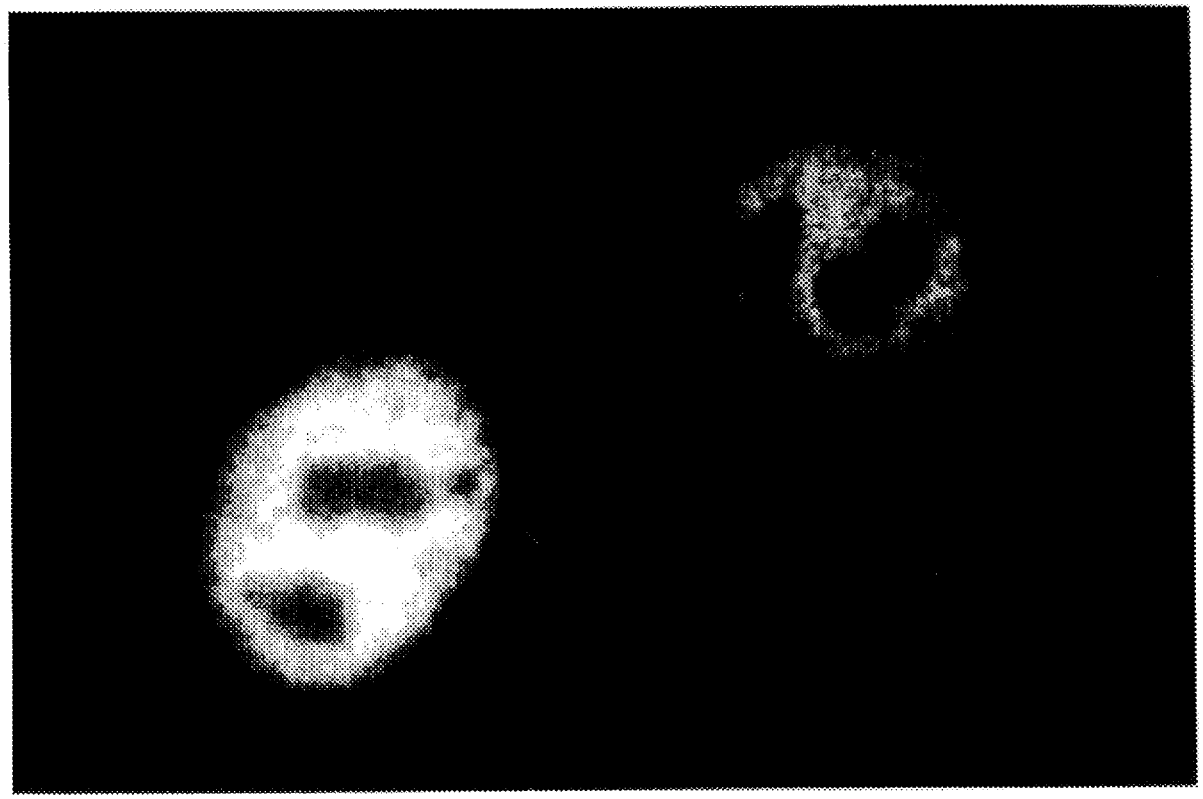

The two types of experiments were performed to ask whether Cdc2 can serve as a substrate of Myt1Hu (FIGS. 4 and 5). In one case, insect cells were co-infected with recombinant baculoviruses encoding Cdc2, cyclin B1 and different concentrations of either human Wee1 (FIG. 4, lanes 2 and 3), human Myt1 (FIG. 4A, lanes 4 and 5) or Xenopus Myt1 (FIG. 4A, lanes 6 and 7). The status of Thr 14 and Tyr 15 phosphorylation of Cdc2 can be assessed by its electrophoretic mobility on SDS gels. A retardation in the electrophoretic mobility of Cdc2 of one increment is due to the phosphorylation of either Thr 14 or Tyr 15. A retardation of two increments is due to phosphorylation at both sites simultaneously. As shown previously, human Wee1 phosphorylates Cdc2 on Tyr 15 only thereby resulting in a single incremental shift (FIG. 4A, lanes 2 and 3), Xenopus Myt1 phosphorylates Cdc2 on both Tyr 15 and Thr 14 thereby resulting in greater retardation in the electrophoretic mobility of Cdc2 (FIG. 4, lanes 6 and 7). Coinfection of Cdc2/ Cyclin B with human Myt1 results in the appearance of two new electrophoretic forms of Cdc2, indicative of Thr 14 and Tyr 15 phosphorylation (FIG. 4, lanes 4). In a second type of experiment components were purified and kinase assays were performed in vitro, resulting in the appearance of two new electrophoretic forms of Cdc2, indicative of Thr 14 and Tyr 15 phosphorylation.

To investigate the subcellular distribution of human Myt1, a myc-tagged version of Myt1Hu was introduced into HeLa cells by transfection. Indirect immunofluorescence using a monoclonal antibody specific to the myc-epitope tag (SEQ ID NO:7) was used to visualize Myt1Hu. As seen in FIGS. 6A–6F, Myt1Hu gave a pattern of fluorescence indicative of an endoplasmic reticulum (ER) localization. Deletion of the C-terminal 97 amino acids of Myt1Hu had no effect on its subcellular distribution. However, a C-terminal deletion of 137 amino acids resulted in the redistribution of Myt1Hu primarily to the nucleus, although a diffuse cytoplasmic staining could also be detected. This suggests that sequences between amino acid 362 and 402 are required for ER localization. Within this segment of 40 residues is a region with a predicted alpha helical structure containing a stretch of 20 hydrophobic or polar amino acids (SEQ ID NO:8) bordered by arginine 378 and histidine 399. A similar domain is conserved in Xenopus Myt1 and likely accounts for the ER localization of human Myt1.

Cloning of an Internal cDNA Fragment of Human Myt1

An internal fragment of the human Myt1 cDNA was cloned using a reverse transcriptase reaction followed by PCR in which degenerate oligonucleotides were used as primers. Primers were designed based on regions of high amino acid conservation between members of the Wee1 family of protein kinases and on the amino acid sequence of Xenopus Myt1 (Mueller, P. R. et al., supra). The nucleotide sequence of each primer is as follows:

Primer #1:
5'CGCCATATG(C/T)(T/A)IGT(I/C)CA(C/T)(A/C/T)TIGA(C/T)(I/C)T(I/C)AA (A/G)CC; (SEQ ID NO:4)

Primer #2:
5'GGACATATGTGCCAI(T/G/C)II(A/T)(C/G)ICC(A/G)TT(I/C)(C/T)(G/T/C)(I/C)GG; (SEQ ID NO:5)

Primer #3:
5'CCGCGGATCC(T/C)(T/G)IAA(A/G)(C/A/T)TIGGIGA(T/C)(T/C)T(I/C)GG. (SEQ ID NO:6)

Total RNA was prepared from Jurkat cells (~2×10$^7$ cells) using a Qiagen Total RNA preparation kit under conditions recommended by the manufacturer (Qiagen, Chatsworth, Calif.) The reverse transcriptase reaction was performed using a Clontech 1st-strand cDNA Synthesis Kit under conditions recommended by the manufacturer using 1.5 μg of total RNA (Clontech Laboratories, Inc., Palo Alto, Calif.).

PCR was then performed on $\frac{1}{10}$ volume of the reverse transcriptase reaction using primer #s 1 and 2. In addition to the template, the reactions (100 μL total volume) contained 150 pmol each of primer #1 and #2, 200 μM dNTPs, and 1X Taq DNA Polymerase Reaction Buffer (final concentrations: 100 mM Tris HCl, pH 8.3; 500 mM KCl; 1.5 mM MgCl$_2$;0.1% (w/v) gelatin). The reactions were heated to 85° C. for 4 min, after which, 1.25 units of Taq DNA Polymerase (Promega, Madison, Wis.) was added. Next, the reactions were cycled 3 times using the following conditions: 94° C. for 30 sec, 37° C. for 30 sec, Ramp to 72° C. for 2 min 30 sec, and 72° C. for 90 sec. Following these initial low stringency cycling conditions, the reactions were cycled 30 times under the following conditions: 94° C. for 45 sec, 50° C. for 30 sec, and 72° C. for 60 sec. The cycling concluded with a final extension phase of 7 min.

A secondary PCR was then performed on an aliquot of the primary PCR product. The reaction conditions were identical to those used in the initial PCR except that 5 μL of the primary PCR served as the template and 150 pmol of primer #3 was used in place of primer #1. The secondary PCR was heated to 94° C. for 2 min 30 sec and then cycled 35 times under the following conditions: 94° C. for 30 sec, 52° C. for 2 min, and 72° C. for 2 min. The cycling concluded with a final extension phase of 7 min. An aliquot (20 μL) of the secondary PCR was then run on a 1.2% agarose gel. A band of approximately 210 base pairs was isolated using a Qiagen Gel Extraction Kit under conditions recommended by the manufacturer (Qiagen, Chatsworth, Calif.). This isolated cDNA fragment was then reamplified using conditions identical to those used in the secondary PCR except that the reactions were cycled only 25 times and the isolated 210 bp fragment served as the template. This final PCR resulted in a single 210 bp product visible by agarose gel-electrophoresis and staining with Ethidium Bromide.

Using the TA Cloning System and conditions recommended by the manufacturer, this cDNA fragment was then directly cloned into the pCR II cloning vector (Invitrogen, San Diego, Calif.). The ligation and transformation resulted in approximately 70 transformants, 24 of which contained a 210 bp insert. Initially, individual transformants were screened by sequence analysis. Subsequently, the Xenopus Myt1 cDNA sequence was published (Muellar, P. R. et al. (1995)) and a sample of the Xenopus Myt1 cDNA was made available by W. Dunphey. In order to expedite the identification of clones containing a portion of the human Myt1 cDNA, 25 ng of each plasmid containing a 210 bp insert was blotted onto a charged nylon membrane (Du Pont-NEN, Boston, Mass.) and then incubated with radiolabeled cDNA probes prepared from the human Wee1 kinase domain (~900 bp Xba I-Acc I fragment) and the Xenopus Myt1 kinase domain. Those clones which hybridized preferentially to the Xenopus Myt1 probe were then sequenced (Applied Biosystems, Perkin-Elmer Corporation, Foster City, Calif.). Conceptional translation of the partial cDNAs indicated 75% sequence identity with a portion of Xenopus Myt1 (residues 253–300; Genbank accession number=U28931).

Isolation of a Full Length Human Myt1 cDNA

The 210 bp PCR product was labeled using the Megaprime DNA Labeling System (Trademark, Amersham) and was used to screen a lambda ZAP II HeLa cDNA library (Stratagene) according to the manufacturer's instructions. A total of 0.68×10$^6$ phage were plated. After growing for 10 hr at 37° C., phage were lifted onto Colony/Plaque Screen nylon membranes (DuPont, NEN). Lysis was accomplished by floating the membranes on solutions consisting of: 0.5N NaOH (twice); followed by 1M Tris (pH 7.5), 1.25M NaCl. Filters were UV-irradiated and prehybridization was performed at 42° C. for 4 hr in 2×PIPES buffer (20 mM PIPES pH 6.5, 0.8M NaCl), 0.5% SDS, 50% formamide, and 100 µg/ml denatured salmon sperm DNA. Labeled probe was added to 1×10$^6$ cpm/ml and hybridization was continued under the conditions described above for 14–16 hr. The membrane filters were then washed twice in 2×SSC, 0.1% SDS for 10 min at room temperature, and once in 0.1 SSC, 0.1% SDS for 15 min at 65° C. Sixteen positive plaques were subjected to two additional rounds of hybridization. pBluescript phagemids containing the cDNA inserts were excised in vivo from the parental lambda ZAP II vector. DNA Sequencing reactions were performed using the Dye Terminator Cycle Sequencing Core Kit (Perkin-Elmer Corporation, Foster City, Calif.) followed by direct automated DNA sequencing.

Human Myt1 Constructs pETHisMyt1: Human Myt1 cDNA was amplified by PCR using the following primers:

Primer N:
5'-CCGGATCCATATGCTAGAACGGCCTCC-3' (SEQ ID NO:9)

Primer C:
5'-CCAGTATCATATGTTAACTCAGGTTGGGTCTA-GGGTGTC-3' (SEQ ID NO:10)

To facilitate cloning, Primer N was designed to contain Bam HI and Nde I sites and Primer C to contain Hpa I and Nde I sites. PCR was carried out using 100 pmole of each primer, 200 mM dNTPs, 1 unit Vent DNA polymerase (New England Biolabs) in the presence of Vent DNA Polymerase Buffer (10 mM KCl, 20 mM Tris HCl (pH 8.8), 10 mM $(NH_4)_2SO_4$, 2 mM $MgSO_4$, 0.1% Triton X-100) supplemented with 10% DMSO. PCR was initiated with three cycles of 94° C. for 1 min (to denature), 48° C. for 1 min (to anneal) and 72° C. for 2 min (to extend), followed by 20 cycles using the following conditions: 94° C. for 1 min; 60° C. for 1 min; 72° C. for 2 min (extension conditions for the 20th cycle were: 72° C. for 5 min). The 1.5 kb PCR product was digested with Nde I and cloned into the Nde I site of pET15b (Novagen).

pFASTBACHisMyt1Hu: pFASTBACHisMyt1 was constructed by subcloning an Xba I-Xho fragment of pETHisMyt1Hu into the Xba I-Xho site of plasmid pFAST-BAC1 (BRL).

pFASTBACMyt1Hu: pFASTBACMyt1Hu was constructed by subcloning a BstE II-Eco fragment of the human Myt1 cDNA (where the BstE II end was blunt-ended with Klenow polymerase), into Bam HI and Eco RI digested pFASTBAC1 (where the Bam HI site was also blunt ended with Klenow polymerase).

pCDNAmycMyt Hu: Human Myt1 CDNA was amplified by PCR using the same cycling conditions described above for PETHisMyt1. Primers were as follows: Primer N-myc:
5'CCGGATCCATATGGAGCAGAAGCTCATCTC AGAAGAAGACCTCCTAGAACGGCCTCCTGC (SEQ ID NO:3) in combination with primer C (see pETHisMyt1 above) The N-myc primer fuses sequences encoding EQK-LISEEDL (myc-epitope tag, underlined above) in frame with N-terminal Myt1 sequences and also contains Bam HI and Nde I sites. The PCR product was digested with Bam HI and cloned into Bam HI and Eco RV digested pCDNA3 vector (Invitrogen).

Northern Analysis A human cancer cell line MTN blot (Clontech) was probed and processed according to the manufacturer's instructions with the following modifications. A 1.2 kb Nco I fragment derived from the human Myt1 cDNA was labeled with ($^{32}$p) α-dCTP using the Megaprime DNA Labeling System (Trademark, Amersham). The MTN blot was prehybridized at 42° C. for 4 hr in buffer containing 5×SSPE, 7×Denhardt's solution, 1% SDS, 50% formamide, and 100 µg/ml denatured salmon sperm DNA (Maniatis et al. 1982). Labeled Myt1 probe was added to 2×10$^6$ cpm/ml and the blot was hybridized for a further 16 hr as described above. The blot was washed twice in 2×SSC, 0.05% SDS at room temperature for 10 min, and twice in 0.1×SSC, 0.1% SDS at 60° C. for 10 min. To probe to actin, the blot was stripped by incubating in 0.5% SDS at 95° C. for 10 min and re-hybridized with labeled human β-actin probe as described above.

Several human cancer cell lines were probed by northern analysis with Myt1Hu cDNA to detect and quantify expression of Myt1Hu mRNA in cells displaying a proliferation disorder. Results are shown in FIG. 1 for: promyelocytic leukemia HL-60 (lane 1), HeLa S3 (lane 2), chronic myelogenous leukemia K-562 (lane 3), lymphoblastic leukemia MOLT-4 (lane 4), Burkitt's lymphoma Raji (lane 5), colorectal adenocarcinoma SW480 (lane 6), lung carcinoma A549 (lane 7) and melanoma G361 (lane 8). As an internal control for constitutive expression levels, the Myt1Hu probe was removed and the same blot was hybridized with a human β-actin probe (bottom panel). The results demonstrate a wide variation of Myt1Hu expression among various cancer cell lines. Aberrant Myt1Hu expression is therefore a characteristic of at least some cancer cell types. The measurement of Myt1Hu expression is therefore a useful diagnostic technique for identifying and characterizing cancers and other pathologies of cell proliferation. Intracellular levels of Myt1Hu can also be detected and quantified by immunoassay techniques, using antibody directed against Myt1Hu. Standard ELISA or radioimmune assays can be employed for measuring Myt1Hu in whole or partially purified cell lysates. Fluorescent antibody can be employed to assess over- or under-expression of Myt1Hu histochemically, as well as to detect aberrant intracellular localization of Myt1Hu.

Preparation of Recombinant Cdc2(K33R) Substrate

Recombinant cyclin B/Cdc2(K33R) complex was purified from insect cells. Approximately 5×10$^8$ insect cells were infected with recombinant baculoviruses encoding Cdc2 (K33R) and GST-cyclin B and harvested at 45 hours post infection. Cells were lysed in 40 ml of NP40/Tris buffer (50 mM Tris pH 7.4, 0.25M NaCl, 5 mM NaF, 10 mM NaPPi, 0.1% NP40) supplemented with protease and phosphatase inhibitors, and lysates were clarified by centrifugation at 27,000×g for 15 min at 4° C. GST-cyclin B/Cdc2(K33R) complexes were precipitated by incubation of the lysate for 1 hour at 4° C. with 20 ml of packed glutathione agarose beads (Sigma Chemical Co.) equilibrated with NP40/Tris buffer. Beads were washed 5× each with NP40Tris buffer, LiCl Buffer and Column Buffer A (25 mM Tris HCl pH 7.5, 1 mM EDTA, 0.01% Brij-35). Beads were then resuspended in 20 ml of Column Buffer A containing 150 mM NaCl, 2.5 mM $CaCl_2$, 20 mM glutathione and 50 units of thrombin (Sigma Chemical Co.) and incubated for 45 min at 25° C. The supernatant was then removed and the beads were washed once with 20 ml buffer A containing 150 mM NaCl and 2.5 mM $CaCl_2$. The two supernatants were pooled and desalted using a 200 ml Sephadex G-25 column (Pharmacia) pre-equilibrated with Column Buffer A supplemented with 50 mM NaCl. The desalted pool was then loaded onto a 1 ml Resource Q column (Pharmacia) pre-equilibrated with Column Buffer A supplemented with 50 mM NaCl. The Resource Q column was washed with 10 ml of Column Buffer A supplemented with 50 mM NaCl and the complex was eluted with 300 mM NaCl in Column Buffer A and 0.50 ml fractions were collected. Peak fractions were pooled, adjusted to 10% glycerol and frozen in aliquots at −80° C.

Kinase Reactions Performed in Vitro

Uninfected Sf9 cells or cells infected with baculovirus encoding hystidine-tagged MytHu were lysed in buffer consisting of 20 mM Tris (pH 7.5), 0.5M NaCl, 0.5% NP-40, 5 mM imidazole and proteinase inhibitors (2 mM PMSF, 10 μg/ml aprotinin, 20 μM leupeptin and 5 μg/ml pepstatin). Lysates were then incubated with nickel-NTA beads (Qiagen). Beads were washed three times with lysis buffer and three times with incomplete kinase buffer (50 mM Tris (pH 7.5), 10 mM $MgCl_2$). Kinase reaction was carried out at 30° C. for 20 min in incomplete kinase buffer supplemented with 2 mM ATP, 1 mM sodium orthovanadate, 1 μM microcystin, and 0.5 μg of purified Cdc2/cyclinB complex. The reaction was stopped by the addition of SDS sample buffer and proteins were resolved on a 12% SDS-polyacrylamide gel. After transfer to nitrocellulose the blot was probed with Cdc2 antisera and developed with an ECL Western blotting detection kit (Amersham).

Phosphorylation of Cdc2 by Myt1Hu in Sf9 cells

Sf9 cells were infected with baculoviruses encoding GST-cyclin B and Cdc2K33R alone or together with two concentrations of baculovirus encoding human p95Weel; human Myt1 or Xenopus Myt1. Cells were washed with PBS 42 hr after infection and lysed in lysis buffer (50 mM Tris (pH 7.4), 250 mM NaCl, 5 mM NaF, 1 mM sodium orthovanadate, 1 μM microcystin and the following proteinase inhibitors: 2 mM PMSF, 10 μg/ml aprotinin, 20 μM leupeptin and 5 μg/ml pepstatin. GST-cyclin B/Cdc2 complexes were precipitated and glutathione agarose beads and washed three times with lithium chloride wash buffer (50 mM Tris (pH 7.5), 0.5M LiCl). Proteins were resolved on a 12% SDS polyacrylamide gel. After transfer to nitrocellulose the blot was probed with Cdc2 antisera and developed with an ECL Western blotting detection kit (Amersham).

Indirect Immunofluorescence

HeLa cells were grown on 12 mm coverslips and transfected with DNA using LipofectAMINE reagent (BRL) in Opti-MEM reduced serum media (BRL) for 4.5 hr and then incubated in Dulbecco's Modified Eagle Medium (DMEM) supplemented with 10% calf serum at 37° C. for 24 hrs. Cells were washed twice with phosphate-buffered saline (PBS) at room temperature and then fixed with 3.7% formaldehyde in PBS for 10 min. Samples were then washed in 50 mM $NH_4Cl$ in PBS for 5 min, twice in PBS, and then permeablized with 0.1% Nonidet P-40 (NP-40) in PBS for 15 min. All subsequent incubations and washes were carried out at room temperature for 5 min. in 0.1% NP-40 and PBS. After blocking with 5% normal donkey serum (Jackson Immuno Research) for 30 min, cells were incubated with secondary antibody for 45 min, washed four times for 15 min each, and mounted on glass slides. When indicated, cells were also treated with 0.1 μg/ml of DAPI.

Primary antibodies were used at the following dilutions: The mAb to Myc epitope (9E10) was used at a 1:200 dilution.

The Cy3-conjugated donkey anti-mouse antibody (Jackson Immuno Research) were used at a 1:500 dilution.

Antibodies to Myt1 Hu were prepared using a peptide antigen composed of the C-terminal 13 amino acids of Myt1 Hu coupled to a cysteine residue at its N-terminus, cross-linked to keyhole limpit hemocyanin. The antigen was used to immunize rabbits according to a standard protocol known in the art. (See, e.g., Harlow and Lane (1988) *Antibodies: A Laboratory Manual*, Cold Spring Harbor Laboratories). Often the C-terminal regions of kinases are not conserved among family members and therefore represent the best candidates for making antibodies with the greatest specificity. Similarly, monoclonal antibodies can be generated from either whole protein or peptide epitopes, using known methods (See, e.g., Goding (1981) *Monoclonal Antibodies: Principles and Practice*, 2d ed., Academic Press, New York). Direct immunoassay methods for measurement of Myt1 Hu protein in cells or cell extracts can be carried out by techniques known in the art.

---

I claim:

1. A DNA sequence encoding the amino acid sequence of Myt1Hu, as set forth in SEQ ID NO:2.

2. A DNA sequence according to claim 1 comprising the nucleotide sequence encoding Myt1Hu set forth in SEQ ID NO:1.

3. A transformed cell comprising a DNA sequence according to claim 1 combined with a heterologous control sequence and expressible in said cell.

4. A transformed cell according to claim 3 wherein said cell is a non-human cell.

5. A transformed cell comprising DNA sequence according to claim 2 combined with a heterologous control sequence and expressible in said cell.

6. A transformed cell according to claim 5 wherein said cell is non-human cell.

\* \* \* \* \*

UNITED STATES PATENT AND TRADEMARK OFFICE
CERTIFICATE OF CORRECTION

PATENT NO. : 5,744,349

DATED : April 28, 1998

INVENTOR(S) : Piwnica-Worms

It is certified that error appears in the above-identified patent and that said Letters Patent is hereby corrected as shown below:

In Col. 9, lines 57 and 58, replace
"5' CCGGATCCATATGGAGCAGAAGCTCATCTCAGAAGAAGACCTCCTAGAACGGCCTCCTGC"
with
--5' CCGGATCCATATG<u>GAGCAGAAGCTCATCTCAGAAGAAGACCTC</u>CTAGAACGGCCTCCTGC--.

In Col. 10, line 3, rewrite "($^{32}P$)" should read --($^{32}P$)--.

Signed and Sealed this

Twentieth Day of October, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 1881 base pairs
        ( B ) TYPE: nucleic acid
        ( C ) STRANDEDNESS: double
        ( D ) TOPOLOGY: Not Relevant ( i i ) MOLECULE TYPE: cDNA to mRNA ( i i i ) HYPOTHETICAL: NO ( i v ) ANTI-SENSE: NO ( i x ) FEATURE:
        ( A ) NAME/KEY: CDS (B) LOCATION: 214..1713

(xi) SEQUENCE DESCRIPTION: SEQ ID NO:1:

```
GATATCGAAT TCCGGAATTC CCCGGGAAAG GTGGCCAGCA GATGTGTCGG GCCTGGTGAG      60

AGGGTGAGGC GAGACGGCCC GATCGCCCAG GGCCCCGGAA GCTGCGGAGG TCACCCCCGC     120

CTGGCCTTAG CTCAGGGACA CCCTGGATTC ACGTGGGAGC CCTGCTCCT  GCCTCCCCG      180

TCCCACCACT GAGGCTGTTG GGCCAGGCCA GTC ATG CTA GAA CGG CCT CCT GCA     234
                                    Met Leu Glu Arg Pro Pro Ala
                                     1               5
```

| | | | | | | | | | | | | | | | | |
|---|---|---|---|---|---|---|---|---|---|---|---|---|---|---|---|---|
| CTG | GCC | ATG | CCC | ATG | CCC | ACG | GAG | GGC | ACC | CCG | CCA | CCT | CTG | AGT | GGC | 282 |
| Leu | Ala | Met | Pro | Met | Pro | Thr | Glu | Gly | Thr | Pro | Pro | Pro | Leu | Ser | Gly | |
|  |  | 10 |  |  |  |  | 15 |  |  |  |  | 20 |  |  |  | |
| ACC | CCC | ATC | CCA | GTC | CCA | GCC | TAC | TTC | CGC | CAC | GCA | GAA | CCT | GGA | TTC | 330 |
| Thr | Pro | Ile | Pro | Val | Pro | Ala | Tyr | Phe | Arg | His | Ala | Glu | Pro | Gly | Phe | |
|  | 25 |  |  |  |  | 30 |  |  |  |  |  | 35 |  |  |  | |
| TCC | CTC | AAG | AGG | CCC | AGG | GGG | CTC | AGC | CGG | AGC | CTC | CCA | CCT | CCG | CCC | 378 |
| Ser | Leu | Lys | Arg | Pro | Arg | Gly | Leu | Ser | Arg | Ser | Leu | Pro | Pro | Pro | Pro | |
| 40 |  |  |  |  | 45 |  |  |  |  | 50 |  |  |  |  | 55 | |
| CCT | GCC | AAG | GGC | AGC | ATT | CCC | ATC | AGC | CGC | CTC | TTC | CCT | CCT | CGG | ACC | 426 |
| Pro | Ala | Lys | Gly | Ser | Ile | Pro | Ile | Ser | Arg | Leu | Phe | Pro | Pro | Arg | Thr | |
|  |  |  |  | 60 |  |  |  |  | 65 |  |  |  |  | 70 |  | |
| CCA | GGC | TGG | CAC | CAG | CTG | CAG | CCC | CGG | CGG | GTG | TCA | TTC | CGG | GGC | GAG | 474 |
| Pro | Gly | Trp | His | Gln | Leu | Gln | Pro | Arg | Arg | Val | Ser | Phe | Arg | Gly | Glu | |
|  |  | 75 |  |  |  |  | 80 |  |  |  |  | 85 |  |  |  | |
| GCC | TCA | GAG | ACT | CTG | CAG | AGC | CCT | GGG | TAT | GAC | CCA | AGC | CGG | CCA | GAG | 522 |
| Ala | Ser | Glu | Thr | Leu | Gln | Ser | Pro | Gly | Tyr | Asp | Pro | Ser | Arg | Pro | Glu | |
|  | 90 |  |  |  |  | 95 |  |  |  |  | 100 |  |  |  |  | |
| TCC | TTC | TTC | CAG | CAG | AGC | TTC | CAG | AGG | CTC | AGC | CGC | CTG | GGC | CAT | GGC | 570 |
| Ser | Phe | Phe | Gln | Gln | Ser | Phe | Gln | Arg | Leu | Ser | Arg | Leu | Gly | His | Gly | |
| 105 |  |  |  |  | 110 |  |  |  |  | 115 |  |  |  |  |  | |
| TCC | TAC | GGA | GAG | GTC | TTC | AAG | GTG | CGC | TCC | AAG | GAG | GAC | GGC | CGG | CTC | 618 |
| Ser | Tyr | Gly | Glu | Val | Phe | Lys | Val | Arg | Ser | Lys | Glu | Asp | Gly | Arg | Leu | |
| 120 |  |  |  |  | 125 |  |  |  |  | 130 |  |  |  |  | 135 | |
| TAT | GCG | GTA | AAG | CGT | TCC | ATG | TCA | CCA | TTC | CGG | GGC | CCC | AAG | GAC | CGG | 666 |
| Tyr | Ala | Val | Lys | Arg | Ser | Met | Ser | Pro | Phe | Arg | Gly | Pro | Lys | Asp | Arg | |
|  |  |  | 140 |  |  |  |  | 145 |  |  |  |  | 150 |  |  | |
| GCC | CGC | AAG | TTG | GCC | GAG | GTG | GGC | AGC | CAC | GAG | AAG | GTG | GGG | CAG | CAC | 714 |
| Ala | Arg | Lys | Leu | Ala | Glu | Val | Gly | Ser | His | Glu | Lys | Val | Gly | Gln | His | |
|  |  | 155 |  |  |  |  | 160 |  |  |  |  | 165 |  |  |  | |
| CCA | TGC | TGC | GTG | CGG | CTG | GAG | CAG | GCC | TGG | GAG | GAG | GGC | GGC | ATC | CTG | 762 |
| Pro | Cys | Cys | Val | Arg | Leu | Glu | Gln | Ala | Trp | Glu | Glu | Gly | Gly | Ile | Leu | |
|  | 170 |  |  |  |  | 175 |  |  |  |  | 180 |  |  |  |  | |
| TAC | CTG | CAG | ACG | GAG | CTG | TGC | GGG | CCC | AGC | CTG | CAG | CAA | CAC | TGT | GAG | 810 |
| Tyr | Leu | Gln | Thr | Glu | Leu | Cys | Gly | Pro | Ser | Leu | Gln | Gln | His | Cys | Glu | |
| 185 |  |  |  |  | 190 |  |  |  |  | 195 |  |  |  |  |  | |
| GCC | TGG | GGT | GCC | AGC | CTG | CCT | GAG | GCC | CAG | GTC | TGG | GGC | TAC | CTG | CGG | 858 |
| Ala | Trp | Gly | Ala | Ser | Leu | Pro | Glu | Ala | Gln | Val | Trp | Gly | Tyr | Leu | Arg | |
| 200 |  |  |  |  | 205 |  |  |  |  | 210 |  |  |  |  | 215 | |
| GAC | ACG | CTG | CTT | GCC | CTG | GCC | CAT | CTG | CAC | AGC | CAG | GGC | CTG | GTG | CAC | 906 |
| Asp | Thr | Leu | Leu | Ala | Leu | Ala | His | Leu | His | Ser | Gln | Gly | Leu | Val | His | |
|  |  |  |  | 220 |  |  |  |  | 225 |  |  |  |  | 230 |  | |
| CTT | GAT | GTC | AAG | CCT | GCC | AAC | ATC | TTC | CTG | GGG | CCC | CGG | GGC | CGC | TGC | 954 |
| Leu | Asp | Val | Lys | Pro | Ala | Asn | Ile | Phe | Leu | Gly | Pro | Arg | Gly | Arg | Cys | |
|  |  |  | 235 |  |  |  |  | 240 |  |  |  |  | 245 |  |  | |
| AAG | CTG | GGT | GAC | TTC | GGA | CTG | CTG | GTG | GAG | CTG | GGT | ACA | GCA | GGA | GCT | 1002 |
| Lys | Leu | Gly | Asp | Phe | Gly | Leu | Leu | Val | Glu | Leu | Gly | Thr | Ala | Gly | Ala | |
|  |  | 250 |  |  |  |  | 255 |  |  |  |  | 260 |  |  |  | |
| GGT | GAG | GTC | CAG | GAG | GGA | GAC | CCC | CGC | TAC | ATG | GCC | CCC | GAG | CTG | CTG | 1050 |
| Gly | Glu | Val | Gln | Glu | Gly | Asp | Pro | Arg | Tyr | Met | Ala | Pro | Glu | Leu | Leu | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| 265 | | | | 270 | | | | | 275 | | | | | | | |
| CAG | GGC | TCC | TAT | GGG | ACA | GCA | GCG | GAT | GTG | TTC | AGT | CTG | GGC | CTC | ACC | 1098 |
| Gln | Gly | Ser | Tyr | Gly | Thr | Ala | Ala | Asp | Val | Phe | Ser | Leu | Gly | Leu | Thr |      |
| 280 | | | | 285 | | | | | 290 | | | | | | 295 | |
| ATC | CTG | GAA | GTG | GCA | TGC | AAC | ATG | GAG | CTG | CCC | CAC | GGT | GGG | GAG | GGC | 1146 |
| Ile | Leu | Glu | Val | Ala | Cys | Asn | Met | Glu | Leu | Pro | His | Gly | Gly | Glu | Gly |      |
| | | | | 300 | | | | | 305 | | | | | 310 | | |
| TGG | CAG | CAG | CTG | CGC | CAG | GGC | TAC | CTG | CCC | CCT | GAG | TTC | ACT | GCC | GGT | 1194 |
| Trp | Gln | Gln | Leu | Arg | Gln | Gly | Tyr | Leu | Pro | Pro | Glu | Phe | Thr | Ala | Gly |      |
| | | | 315 | | | | | 320 | | | | | 325 | | | |
| CTG | TCT | TCC | GAG | CTG | CGT | TCT | GTC | CTT | GTC | ATG | ATG | CTG | GAG | CCA | GAC | 1242 |
| Leu | Ser | Ser | Glu | Leu | Arg | Ser | Val | Leu | Val | Met | Met | Leu | Glu | Pro | Asp |      |
| | | 330 | | | | | 335 | | | | | 340 | | | | |
| CCC | AAG | CTG | CGG | GCC | ACG | GCC | GAG | GCC | CTG | CTG | GCA | CTG | CCT | GTG | TTG | 1290 |
| Pro | Lys | Leu | Arg | Ala | Thr | Ala | Glu | Ala | Leu | Leu | Ala | Leu | Pro | Val | Leu |      |
| | 345 | | | | 350 | | | | | 355 | | | | | | |
| AGG | CAG | CCG | CGG | GCC | TGG | GGT | GTG | CTG | TGG | TGC | ATG | GCA | GCG | GAG | GCC | 1338 |
| Arg | Gln | Pro | Arg | Ala | Trp | Gly | Val | Leu | Trp | Cys | Met | Ala | Ala | Glu | Ala |      |
| 360 | | | | | 365 | | | | | 370 | | | | | 375 | |
| CTG | AGC | CGA | GGG | TGG | GCC | CTG | TGG | CAG | GCC | CTG | CTT | GCC | CTG | CTC | TGC | 1386 |
| Leu | Ser | Arg | Gly | Trp | Ala | Leu | Trp | Gln | Ala | Leu | Leu | Ala | Leu | Leu | Cys |      |
| | | | | 380 | | | | | 385 | | | | | 390 | | |
| TGG | CTC | TGG | CAT | GGG | CTG | GCT | CAC | CCT | GCC | AGC | TGG | CTA | CAG | CCC | CTG | 1434 |
| Trp | Leu | Trp | His | Gly | Leu | Ala | His | Pro | Ala | Ser | Trp | Leu | Gln | Pro | Leu |      |
| | | | 395 | | | | | 400 | | | | | 405 | | | |
| GGC | CCG | CCA | GCC | ACC | CCG | CCT | GGC | TCA | CCA | CCC | TGC | AGT | TTG | CTC | CTG | 1482 |
| Gly | Pro | Pro | Ala | Thr | Pro | Pro | Gly | Ser | Pro | Pro | Cys | Ser | Leu | Leu | Leu |      |
| | | 410 | | | | | 415 | | | | | 420 | | | | |
| GAC | AGC | AGC | CTC | TCC | AGC | AAC | TGG | GAT | GAC | GAC | AGC | CTA | GGG | CCT | TCA | 1530 |
| Asp | Ser | Ser | Leu | Ser | Ser | Asn | Trp | Asp | Asp | Asp | Ser | Leu | Gly | Pro | Ser |      |
| | 425 | | | | | 430 | | | | | 435 | | | | | |
| CTC | TCC | CCT | GAG | GCT | GTC | CTG | GCC | CGG | ACT | GTG | GGG | AGC | ACC | TCC | ACC | 1578 |
| Leu | Ser | Pro | Glu | Ala | Val | Leu | Ala | Arg | Thr | Val | Gly | Ser | Thr | Ser | Thr |      |
| 440 | | | | | 445 | | | | | 450 | | | | | 455 | |
| CCC | CGG | AGC | AGG | TGC | ACA | CCC | AGG | GAT | GCC | CTG | GAC | CTA | AGT | GAC | ATC | 1626 |
| Pro | Arg | Ser | Arg | Cys | Thr | Pro | Arg | Asp | Ala | Leu | Asp | Leu | Ser | Asp | Ile |      |
| | | | | 460 | | | | | 465 | | | | | 470 | | |
| AAC | TCA | GAG | CCT | CCT | CGG | GGC | TCC | TTC | CCC | TCC | TTT | GAG | CCT | CGG | AAC | 1674 |
| Asn | Ser | Glu | Pro | Pro | Arg | Gly | Ser | Phe | Pro | Ser | Phe | Glu | Pro | Arg | Asn |      |
| | | 475 | | | | | 480 | | | | | 485 | | | | |
| CTC | CTC | AGC | CTG | TTT | GAG | GAC | ACC | CTA | GAC | CCA | ACC | TGA | GCCCCAGACT | | | 1723 |
| Leu | Leu | Ser | Leu | Phe | Glu | Asp | Thr | Leu | Asp | Pro | Thr | * | | | | |
| | | 490 | | | | | 495 | | | | | 500 | | | | |

CTGCCTCTGC ACTTTTAACC TTTTATCCTG TGTCTCTCCC GTCGCCCTTG AAAGCTGGGG    1783

CCCCTCGGGA ACTCCCATGG TCTTCTCTGC CTGGCCGTGT CTAATAAAAA GTATTTGAAC    1843

CTTGGGAGCA CCCAAGCTTG CTCATGTGGC GGAATTCC                            1881

( 2 ) INFORMATION FOR SEQ ID NO:2:

( i ) SEQUENCE CHARACTERISTICS:
      ( A ) LENGTH: 499 amino acids
      ( B ) TYPE: amino acid
      ( D ) TOPOLOGY: linear ( i i ) MOLECULE TYPE: protein ( x i ) SEQUENCE DESCRIPTION: SEQ ID NO:2:

| Met | Leu | Glu | Arg | Pro | Pro | Ala | Leu | Ala | Met | Pro | Met | Pro | Thr | Glu | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Thr | Pro | Pro | Pro | Leu | Ser | Gly | Thr | Pro | Ile | Pro | Val | Pro | Ala | Tyr | Phe |

-continued

```
                        20                          25                          30
Arg  His  Ala  Glu  Pro  Gly  Phe  Ser  Leu  Lys  Arg  Pro  Arg  Gly  Leu  Ser
          35                          40                         45

Arg  Ser  Leu  Pro  Pro  Pro  Pro  Ala  Lys  Gly  Ser  Ile  Pro  Ile  Ser
     50                         55                        60

Arg  Leu  Phe  Pro  Pro  Arg  Thr  Pro  Gly  Trp  His  Gln  Leu  Gln  Pro  Arg
65                       70                        75                          80

Arg  Val  Ser  Phe  Arg  Gly  Glu  Ala  Ser  Glu  Thr  Leu  Gln  Ser  Pro  Gly
                    85                        90                        95

Tyr  Asp  Pro  Ser  Arg  Pro  Glu  Ser  Phe  Gln  Gln  Ser  Phe  Gln  Arg
               100                      105                     110

Leu  Ser  Arg  Leu  Gly  His  Gly  Ser  Tyr  Gly  Glu  Val  Phe  Lys  Val  Arg
          115                     120                      125

Ser  Lys  Glu  Asp  Gly  Arg  Leu  Tyr  Ala  Val  Lys  Arg  Ser  Met  Ser  Pro
     130                     135                     140

Phe  Arg  Gly  Pro  Lys  Asp  Arg  Ala  Arg  Lys  Leu  Ala  Glu  Val  Gly  Ser
145                      150                     155                           160

His  Glu  Lys  Val  Gly  Gln  His  Pro  Cys  Cys  Val  Arg  Leu  Glu  Gln  Ala
               165                     170                          175

Trp  Glu  Glu  Gly  Gly  Ile  Leu  Tyr  Leu  Gln  Thr  Glu  Leu  Cys  Gly  Pro
               180                     185                     190

Ser  Leu  Gln  Gln  His  Cys  Glu  Ala  Trp  Gly  Ala  Ser  Leu  Pro  Glu  Ala
          195                     200                     205

Gln  Val  Trp  Gly  Tyr  Leu  Arg  Asp  Thr  Leu  Leu  Ala  Leu  Ala  His  Leu
     210                     215                     220

His  Ser  Gln  Gly  Leu  Val  His  Leu  Asp  Val  Lys  Pro  Ala  Asn  Ile  Phe
225                      230                     235                          240

Leu  Gly  Pro  Arg  Gly  Arg  Cys  Lys  Leu  Gly  Asp  Phe  Gly  Leu  Leu  Val
                    245                     250                     255

Glu  Leu  Gly  Thr  Ala  Gly  Ala  Gly  Glu  Val  Gln  Glu  Gly  Asp  Pro  Arg
               260                     265                     270

Tyr  Met  Ala  Pro  Glu  Leu  Leu  Gln  Gly  Ser  Tyr  Gly  Thr  Ala  Ala  Asp
          275                     280                     285

Val  Phe  Ser  Leu  Gly  Leu  Thr  Ile  Leu  Glu  Val  Ala  Cys  Asn  Met  Glu
     290                     295                     300

Leu  Pro  His  Gly  Gly  Glu  Gly  Trp  Gln  Gln  Leu  Arg  Gln  Gly  Tyr  Leu
305                      310                     315                          320

Pro  Pro  Glu  Phe  Thr  Ala  Gly  Leu  Ser  Ser  Glu  Leu  Arg  Ser  Val  Leu
               325                          330                     335

Val  Met  Met  Leu  Glu  Pro  Asp  Pro  Lys  Leu  Arg  Ala  Thr  Ala  Glu  Ala
               340                     345                     350

Leu  Leu  Ala  Leu  Pro  Val  Leu  Arg  Gln  Pro  Arg  Ala  Trp  Gly  Val  Leu
          355                     360                     365

Trp  Cys  Met  Ala  Ala  Glu  Ala  Leu  Ser  Arg  Gly  Trp  Ala  Leu  Trp  Gln
     370                     375                     380

Ala  Leu  Leu  Ala  Leu  Leu  Cys  Trp  Leu  Trp  His  Gly  Leu  Ala  His  Pro
385                      390                     395                          400

Ala  Ser  Trp  Leu  Gln  Pro  Leu  Gly  Pro  Ala  Thr  Pro  Pro  Gly  Ser
               405                     410                          415

Pro  Pro  Cys  Ser  Leu  Leu  Leu  Asp  Ser  Ser  Leu  Ser  Ser  Asn  Trp  Asp
               420                     425                     430

Asp  Asp  Ser  Leu  Gly  Pro  Ser  Leu  Ser  Pro  Glu  Ala  Val  Leu  Ala  Arg
               435                     440                     445
```

| Thr | Val | Gly | Ser | Thr | Ser | Thr | Pro | Arg | Ser | Arg | Cys | Thr | Pro | Arg | Asp |
|---|---|---|---|---|---|---|---|---|---|---|---|---|---|---|---|
| | 450 | | | | | 455 | | | | | 460 | | | | |

| Ala | Leu | Asp | Leu | Ser | Asp | Ile | Asn | Ser | Glu | Pro | Pro | Arg | Gly | Ser | Phe |
|---|---|---|---|---|---|---|---|---|---|---|---|---|---|---|---|
| 465 | | | | | 470 | | | | | 475 | | | | | 480 |

| Pro | Ser | Phe | Glu | Pro | Arg | Asn | Leu | Leu | Ser | Leu | Phe | Glu | Asp | Thr | Leu |
|---|---|---|---|---|---|---|---|---|---|---|---|---|---|---|---|
| | | | | 485 | | | | | 490 | | | | | 495 | |

Asp Pro Thr ( 2 ) INFORMATION FOR SEQ ID NO:3:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( x i ) SEQUENCE DESCRIPTION: SEQ ID NO:3:

CCGGATCCAT ATGGAGCAGA AGCTCATCTC AGAAGAAGAC CTCCTAGAAC GGCCTCCTGC     60

( 2 ) INFORMATION FOR SEQ ID NO:4:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: NO ( i x ) FEATURE:
        ( A ) NAME/KEY: misc_feature
        ( B ) LOCATION: 1..32
        ( D ) OTHER INFORMATION: /note="At position 12 N is inosine
            and at the remaining positions N is inosine or cytosine."

( x i ) SEQUENCE DESCRIPTION: SEQ ID NO:4:

CGCCATATGY WNGTNCAYHT NGAYNTNAAR CC     32

( 2 ) INFORMATION FOR SEQ ID NO:5:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: NO ( i x ) FEATURE:
        ( A ) NAME/KEY: misc_feature
        ( B ) LOCATION: 1..32
        ( D ) OTHER INFORMATION: /note="At positions 15, 17, 18 and
            21 N is inosine and at the remaining positions N is
            inosine or cytosine."

( x i ) SEQUENCE DESCRIPTION: SEQ ID NO:5:

GGACATATGT GCCANBNNWS NCCRTTNYBN GG     32

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: NO ( i x ) FEATURE:
        ( A ) NAME/KEY: misc_feature
        ( B ) LOCATION: 1..30
        ( D ) OTHER INFORMATION: /note="At positions 13, 19, and 22, N is inosine and at position 28, N is inosine or cytosine."

( x i ) SEQUENCE DESCRIPTION: SEQ ID NO:6:

```
CCGCGGATCC YKNAARHTNG GNGAYYTNGG                                    30
```

( 2 ) INFORMATION FOR SEQ ID NO:7:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( x i ) SEQUENCE DESCRIPTION: SEQ ID NO:7:

```
Glu  Gln  Lys  Leu  Ile  Ser  Glu  Glu  Asp  Leu
1                  5                        10
```

( 2 ) INFORMATION FOR SEQ ID NO:8:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( x i ) SEQUENCE DESCRIPTION: SEQ ID NO:8:

```
Gly  Trp  Ala  Leu  Trp  Gln  Ala  Leu  Leu  Ala  Leu  Leu  Cys  Trp  Leu  Trp
1                  5                        10                       15
His  Gly  Leu  Ala
            20
```

( 2 ) INFORMATION FOR SEQ ID NO:9:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( x i ) SEQUENCE DESCRIPTION: SEQ ID NO:9:

```
CCGGATCCAT ATGCTAGAAC GGCCTCC                                       27
```

(2) INFORMATION FOR SEQ ID NO:10:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO:10:

```
CCAGTATCAT ATGTTAACTC AGGTTGGGTC TAGGGTGTC                    39
```